United States Patent
Sa et al.

(10) Patent No.: US 10,392,451 B2
(45) Date of Patent: Aug. 27, 2019

(54) LIGAND COMPOUND, ORGANIC CHROMIUM COMPOUND, CATALYST SYSTEM FOR OLEFIN OLIGOMERIZATION, AND METHOD FOR OLIGOMERIZING OLEFINS USING THE SAME THEREOF

(71) Applicant: LG CHEM, LTD., Seoul (KR)

(72) Inventors: Seok Pil Sa, Daejeon (KR); Yong Ho Lee, Daejeon (KR); Eun Ji Shin, Daejeon (KR); Ki Soo Lee, Daejeon (KR); Jin Young Park, Daejeon (KR); Seul Ki Im, Daejeon (KR)

(73) Assignee: LG Chem, Ltd., Seoul (KR)

( * ) Notice: Subject to any disclaimer, the term of this patent is extended or adjusted under 35 U.S.C. 154(b) by 76 days.

(21) Appl. No.: 15/566,120

(22) PCT Filed: Dec. 21, 2015

(86) PCT No.: PCT/KR2015/014032
§ 371 (c)(1),
(2) Date: Oct. 12, 2017

(87) PCT Pub. No.: WO2016/200000
PCT Pub. Date: Dec. 15, 2016

(65) Prior Publication Data
US 2018/0086860 A1 Mar. 29, 2018

(30) Foreign Application Priority Data

Jun. 12, 2015 (KR) .................. 10-2015-0083650
Dec. 18, 2015 (KR) .................. 10-2015-0182257

(51) Int. Cl.
| | | |
|---|---|---|
| C08F 4/69 | (2006.01) | |
| C07F 9/90 | (2006.01) | |
| C07F 11/00 | (2006.01) | |
| C07F 9/46 | (2006.01) | |
| C07C 2/08 | (2006.01) | |
| C07F 7/00 | (2006.01) | |
| C07F 9/00 | (2006.01) | |

(52) U.S. Cl.
CPC ............... *C08F 4/69* (2013.01); *C07C 2/08* (2013.01); *C07F 7/003* (2013.01); *C07F 9/005* (2013.01); *C07F 9/46* (2013.01); *C07F 9/90* (2013.01); *C07F 11/00* (2013.01)

(58) Field of Classification Search
CPC .. C07F 7/90; C07F 7/003; C07F 9/005; C07F 9/46; C07F 11/00; C07C 2/08; C08F 4/69; C08F 10/02; C08F 4/69086
USPC ....................................... 526/106
See application file for complete search history.

(56) References Cited

U.S. PATENT DOCUMENTS

| | | |
|---|---|---|
| 7,141,633 B2 | 11/2006 | Wass |
| 7,511,183 B2 | 3/2009 | Blann et al. |
| 7,786,336 B2 | 8/2010 | Zhang et al. |
| 7,829,749 B2 | 11/2010 | Gao et al. |
| 7,964,763 B2 | 6/2011 | Dixon et al. |
| 8,309,779 B2 | 11/2012 | Han et al. |
| 8,778,827 B2 | 7/2014 | Aliyev et al. |
| 2003/0166456 A1 | 9/2003 | Wass |
| 2005/0020788 A1 | 1/2005 | Wass |
| 2006/0293546 A1* | 12/2006 | Nabika ............... C07C 2/36 585/520 |
| 2007/0232481 A1 | 10/2007 | Zhang et al. |
| 2010/0137669 A1 | 6/2010 | Han et al. |
| 2010/0190939 A1 | 7/2010 | Fritz et al. |
| 2012/0172645 A1 | 7/2012 | Sydora |
| 2012/0310025 A1 | 12/2012 | Wang et al. |
| 2014/0081064 A1 | 3/2014 | Han et al. |
| 2014/0179970 A1 | 6/2014 | Fritz et al. |
| 2015/0361118 A1 | 12/2015 | Lee et al. |
| 2017/0158582 A1 | 6/2017 | Lee et al. |

FOREIGN PATENT DOCUMENTS

| | | |
|---|---|---|
| CN | 1651142 A | 8/2005 |
| CN | 103285926 A | 9/2013 |
| EP | 3118227 A1 | 1/2017 |
| JP | 2006-511625 A | 4/2006 |
| JP | 2006-511694 A | 4/2006 |
| JP | 2018-508591 A | 3/2018 |
| KR | 10-2005-0100600 A | 10/2005 |
| KR | 10-2008-0068226 A | 7/2008 |
| KR | 10-2008-0068227 A | 7/2008 |
| KR | 10-0845444 B1 | 7/2008 |
| KR | 10-2010-0046170 A | 5/2010 |
| KR | 10-2013-0142151 A | 12/2013 |
| KR | 10-1445431 B1 | 9/2014 |
| WO | 2004-056478 A1 | 7/2004 |
| WO | 2004-056480 A1 | 7/2004 |
| WO | 2008/004986 A1 | 1/2008 |
| WO | 2015046965 A1 | 4/2015 |

OTHER PUBLICATIONS

Chem. Comm, The Royal Society of Chemistry, "Highly selective chromium-based ethylene trimerisation catalysts with bulky disphosphinoamine ligands," 2005, pp. 620-621.

* cited by examiner

*Primary Examiner* — William K Cheung
(74) *Attorney, Agent, or Firm* — Dentons US LLP

(57) ABSTRACT

The present invention relates to a ligand compound, catalyst system for olefin oligomerization, and a method for oligomerizing olefins using the same. The catalyst system for olefin oligomerization according to the present invention exhibit selectivity to 1-hexene or 1-octene while having excellent catalytic activity, thus enabling more efficient preparation of alpha-olefins.

13 Claims, No Drawings

LIGAND COMPOUND, ORGANIC CHROMIUM COMPOUND, CATALYST SYSTEM FOR OLEFIN OLIGOMERIZATION, AND METHOD FOR OLIGOMERIZING OLEFINS USING THE SAME THEREOF

CROSS-REFERENCE TO RELATED APPLICATION(S)

This application is a National Stage Entry of International Application No. PCT/KR2015/014032, filed on Dec. 21, 2015, and claims the benefit of and priority to Korean Application No. 10-2015-0083650 filed on Jun. 12, 2015, and Korean Application No. 10-2015-0182257 filed on Dec. 18, 2015 all of which are hereby incorporated by reference in their entirety for all purposes as if fully set forth herein.

TECHNICAL FIELD

The present invention relates to a ligand compound, an organic chromium compound, a catalyst system for olefin oligomerization containing the ligand compound or the organic chromium compound, and a method for oligomerizing olefins using the same.

BACKGROUND OF ART

Linear alpha-olefins such as 1-hexene, 1-octene, and like are used in detergents, lubricants, plasticizers, and so on, and in particular, they are widely used as comonomers for controlling the density of a polymer during the preparation of linear low-density polyethylene (LLDPE).

Such linear alpha-olefins were mainly produced through a Shell Higher Olefin Process. However, since the above process synthesizes alpha-olefins of various lengths simultaneously in accordance with Schultz-Flory distribution, there was an inconvenience of requiring an additional separation step in order to obtain a specific alpha-olefin.

To solve this problem, a method of selectively synthesizing 1-hexene through a trimerization reaction of ethylene or a method of selectively synthesizing 1-octene through a tetramerization reaction of ethylene has been proposed. Further, various studies have been conducted on a catalyst system enabling such selective oligomerization of ethylene.

DETAILED DESCRIPTION OF THE INVENTION

Technical Problem

It is an object of the present invention to provide a novel ligand compound capable of exhibiting high catalytic activity and selectivity in olefin oligomerization reaction.

It is another object of the present invention to provide novel organic chromium compound capable of exhibiting high catalytic activity and selectivity in olefin oligomerization reaction.

It is still another object of the present invention to provide a catalyst system for olefin oligomerization containing the ligand compound or the organic chromium compound.

It is a further object of the present invention to provide a method for oligomerizing olefins using the catalyst system.

Technical Solution

One embodiment of the present invention provides a ligand compound containing at least one group represented by the following chemical formula 1 in a molecule:

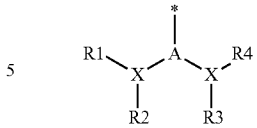

[Chemical Formula 1]

in Chemical Formula 1,

\* means that the group represented by Chemical Formula 1 is a radical,

A is boron (B), nitrogen (N), phosphorus (P) or antimony (Sb), each X is independently phosphorus (P), arsenic (As), or antimony (Sb), $R_1$ to $P_4$ are each independently an aryl group having 6 to 20 carbon atoms in which at least one substituent selected from the group consisting of an alkyl group, an alkoxy group, an alkylsulfanyl group and an alkylsilyl group is optionally substituted or bonded at the meta or pare position.

Another embodiment of the present invention provides an organic chromium compound comprising the ligand compound and chromium (Cr).

Still another embodiment of the present invention provides a catalyst system for olefin oligomerization comprising the above-described ligand compound, a source of chromium, and a cocatalyst.

A further embodiment of the present invention provides a method for oligomerizing olefins comprising the step of performing an oligomerization reaction of olefins in the presence of the above-described catalyst system to form alpha-olefins.

Advantageous Effects

One embodiment of the present invention provides a ligand compound containing a catalyst system for olefin oligomerization according to the present invention exhibits high selectivity to 1-hexene or 1-octene while having excellent catalytic activity, thus enabling more efficient preparation of alpha-olefins.

DETAILED DESCRIPTION OF THE EMBODIMENTS

Hereinafter, the ligand compound, the organic chromium compound, the catalyst system for olefin oligomerization, and the method for oligomerizing an olefin using the same according to the embodiments of the present invention will be described in more detail.

Technical terms used in the present specification are only for mentioning specific embodiments, and they are not intended to restrict the present invention unless there is a particular mention about them. The singular expressions used herein may include plural expressions unless the context explicitly indicate otherwise. The terms such as "including", "comprising", or "having" as used herein are intended to embody specific features, numbers, steps, components, and/or combinations thereof, and does not exclude existence or addition of other specific features, numbers, steps, components, and/or comninations thereof.

As the present invention allows for various changes and numerous embodiments, particular embodiments will be illustrated and described in detail below. However, this is not intended to limit the present invention to particular modes of practice, and it is to be appreciated that all changes, equivalents, and substitutes that do not depart from the spirit and technical scope of the present invention are encompassed in the present invention.

In the present specification, "catalyst system" means what can be obtained as the catalyst composition having activity by mixing three components including a source of chromium, a ligand compound, and a cocatalyst, or alternatively two components of an organic chromium compound and a cocatalyst, at the same time or in an arbitrary order. Said three components or two components of the catalyst system may be mixed in the presence or absence of a proper solvent and a monomer, and it may be used in the form of being supported or unsupported.

According to one aspect of the present invention, there is provided a ligand compound containing at least one group represented by the following chemical formula in a molecule:

[Chemical Formula 1]

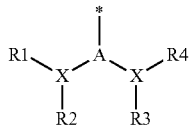

in Chemical Formula 1,

* means that the group represented by Chemical Formula 1 is a radical,

A is boron (B), nitrogen (N), phosphorus (P) or antimony (Sb), each X is independently phosphorus (P), arsenic (As), or antimony (Sb), $R_1$ to $R_4$ are each independently an aryl group having 6 to 20 carbon atoms in which at least one substituent selected from the group consisting of an alkyl group, an alkoxy group, an alkylsulfanyl group and an alkylsilyl group is optionally substituted or bonded at the meta or para position.

As the results of successive experiments of the present inventors, it has been found that, when the ligand compound is applied to a catalyst system for olefin oligomerization, it exhibits excellent selectivity to 1-hexene or 1-octene while exhibiting excellent catalytic activity, thus enabling more efficient preparation of alpha-olefins.

According to one embodiment of the present invention, the ligand compound includes a group represented by Chemical Formula 1 (particularly, a diphosphino aminyl moiety) in the molecule, in which the terminal of the diphosphino aminyl moiety is connected with a aryl group having a specific substituent, thereby providing a form capable of acting as a strong electron donating group by itself.

Due to these structural features, the ligand compounds can be applied to a catalyst system for olefin oligomerization and thus exhibit high oligomerization reaction activity, and in particula exhibit high selectivity to 1-hexene, 1-octene and the like. This can be seen to be attributed to the interaction between the respective adjacent chromium active sites. Especially when aryl substituted or linked by a speclfic substituent is connected to phosphorus (P) atom of the diphosphino aminyl group, the electron density increases at the phosphorus (P) atom and the nitrogen (N) atom included in the diphosphinoaminyl group, and the electrical and steric properties of the entire ligand compound may change.

As a result, the bond between the ligand and the chromium atom is changed, and so the structure of the catalyst can be more stabilized. Further, the energy of the transition state, that is, the activation energy of the reaction, is changed, by allowing the formation of alpha-olefins with higher activity and selectivity, compared to conventional metallacycloheptane or metallacyclononane forms, and it becomes possible to further reduce the amount of by-products such as high molecular weight solid alpha-olefins such as PE wax.

Furthermore, the amount of the 1-hexene isomer which greatly affects the product even in a small amount in the oligomerization reaction can be greatly reduced and, incidentally, separation may be unnecessary due to increase of 1-hexene and decrease of 1-hexene isomer, thereby bringing about an energy saving effect.

Meanwhile, according to one embodiment of the present invention, each X in Chemical Formula 1 may be independently phosphorus (P), arsenic (As) or antimony (Sb). Preferably, the group represented by Chemical Formula 1 may be a diphosphino aminyl moiety in which each X is phosphdrus (P).

In Chemical Formula 1, $R_1$ to $R_4$ are an aryl group having 6 to 20 carbon atoms in which at least one substituent selected from the group consisting of an alkyl group, an alkoxy group, an alkylsulfanyl group, and an alkylsilyl group is substituted or bonded.

More specifically, $R_1$ to $R_4$ in Chemical Formula 1 may be each independently an aryl group having 6 to 20 carbon atoms in which at least one substituent selected from the group consisting of an alkyl group having 1 to 10 carbon atoms, an alkoxy group having 1 to 10 carbon atoms, an alkylsulfanyl group having 1 to 10 carbon atoms and an alkylsilyl group having 1 to 10 carbon atoms is substituted or bonded.

As for the substitution type of $R_1$ to $R_4$, more specifically, $R_1$ to $R_4$ are each independently a phenyl group having 6 to 20 carbon atoms in total, in which only one of the meta positions of the X-linking moiety is substituted or bonded by at least one substituent selected from the group consisting of an alkyl group having 1 to 10 carbon atoms, an alkoxy group having 1 to 10 carbon atoms, an alkylsulfanyl group having 1 to 10 carbon atoms, and an alkylsilyl group having 1 to 10 carbon atoms.

Alternatively, $R_1$ to $R_4$ are each independently a phenyl group having 6 to 20 carbon atoms in total, in which at least two of the meta- and para-positions of the X-linking moiety is substituted or bonded by at least one substituent selected from the group consisting of an alkyl group having 1 to 10 carbon atoms, an alkoxy group having 1 to 10 carbon atoms, an alkylsulfanyl group having 1 to 10 carbon atoms, and an alkylsilyl group having 1 to 10 carbon atoms.

According to an embodiment of the present invention, X in Chemical Formula 1 is phosphorus (P), and the moieties represented by $(R^1)(R^2)X—$ and $(R^3)(R^4)X—$ in Chemical Formula 1 may be represented by the following structural formulas, but are not limited thereto.

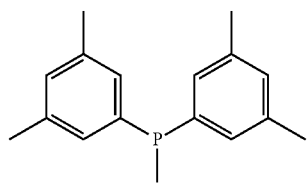

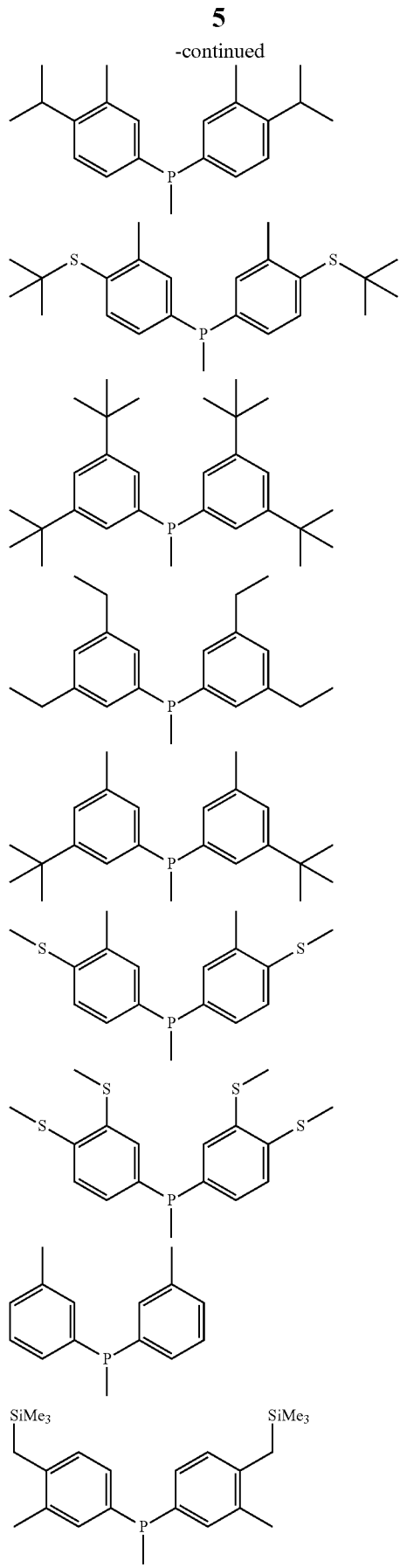

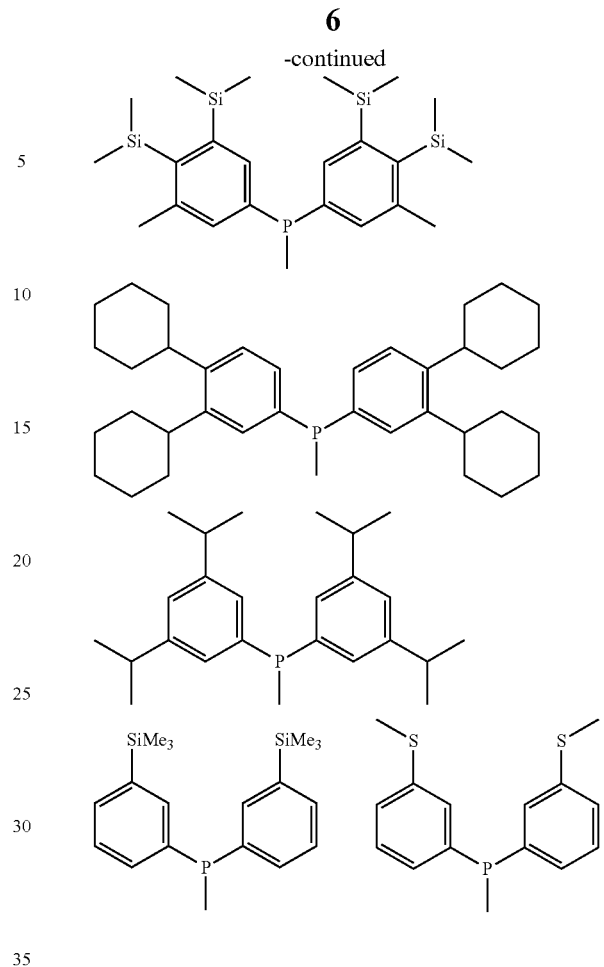

In addition, two or more groups represented by Chemical Formula 1 may be included in one compound. In this case, the linker connecting the two groups may include an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or the aliphatic group, the heteroaliphatic group, the alicyclic group, and the heteroalicyclic group. More specifically, by way of a non-limiting example, the linker may be an aliphatic group having 2 to 8 carbon atoms (for example, an alkylene group, an alkenylene group, an alkynylene group or a heteroaliphatic group containing a hetero atom in the aliphatic group), an alicyclic group having 2 to 20 carbon atoms (for example, a cycloalkylene group, a cycloalkenylene group, a cycloalkynylene group, or a heteroalicyclic group containing a heteroatom in the alicyclic group), in which 2 to 8 carbon atoms is linked between two or more groups represented by Chemical Formula 1, or a form in which the aliphatic (or heteroaliphatic) group and the alicyclic (or heteroalicyclic) group are bonded.

Non-limiting examples of the above-described ligand compound may include a compound having the following structure. In the examples below, the group represented by Chemical Formula 1 is represented by [A], [A'] or [A"] for convenience, and [A], [A'] and [A]] may be the same or different.

(i) a compound having a group linking two or three carbon atoms between a plurality of A:

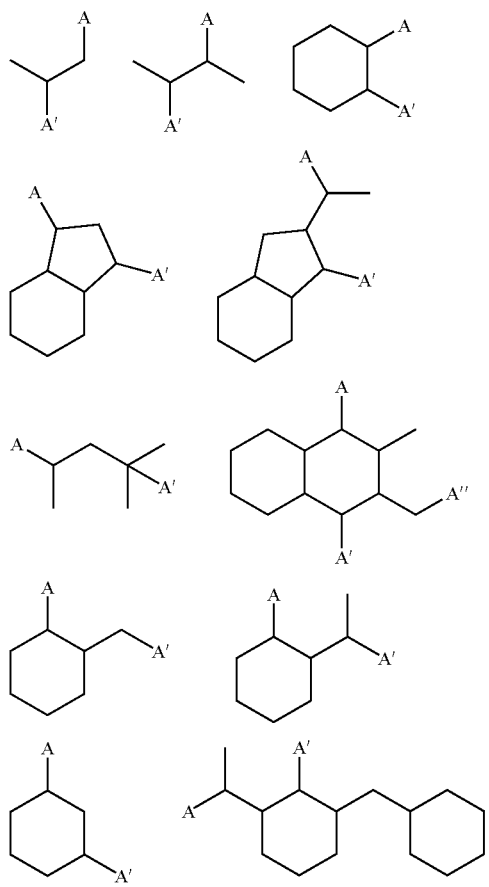

(ii) a compound having a group linking four carbon atoms between a plurality of A:

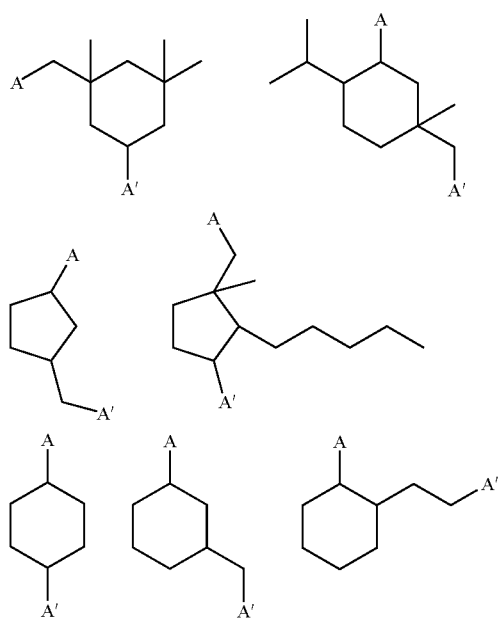

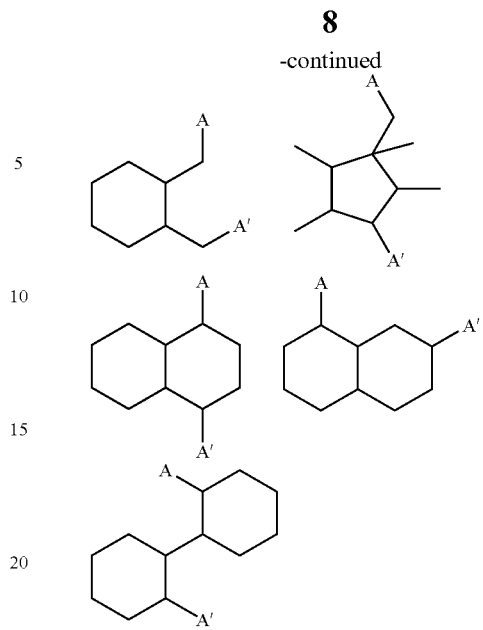

(iii) a compound having a group linking five or more carbon atoms between a plurality of A:

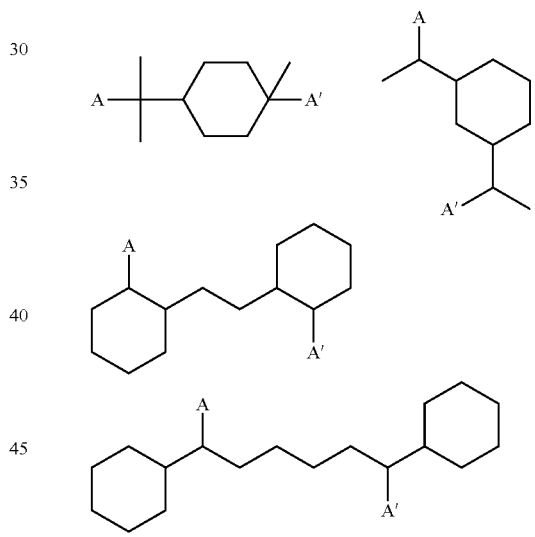

The ligand compound according to the present invention may be implemented by various combinations in the range satisfying the above-mentioned conditions in addition to the compounds of the above examples. And, the ligand compound can be synthesized by applying known reactions, and the detailed synthesis method will be described in detail in Examples section.

Meanwhile, according to another aspect of the present invention, there is provided an organic chromium compound including the above mentioned ligand compound and chromium (Cr).

The organic chromium compound may be a compound having a chromium atom as a central metal in which the aforementioned ligand compound is coordinated, and may include, for example, a group represented by the following chemical formula 1-1.

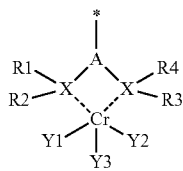

[Chemical Formula 1-1]

in Chemical Formula 1-1,

\* means that the group represented by Chemical Formula 1-1 is a radical,

A is boron (B), nitrogen (N), phosphorus (P) or antimony (Sb), each x is independently phosphorus (P), arsenic (As), or antimony (Sb), $R_1$ to $R_4$ are each independently an aryl group having 6 to 20 carbon atoms in which at least one substituent selected from the group consisting of an alkyl group, an alkoxy group, an alkylsulfanyl group and an alkylsilyl group is optionally substituted or bonded at meta or para position;

Cr is chromium, and $Y_1$ to $Y_3$ are each independently a halogen, a hydrogen, a hydrocarbyl having 1 to 10 carbon atoms, or a heterohydrocarbyl having 1 to 10 carbon atoms.

The organic chromium compound may be a chromium complex compound of the above-mentioned ligand compound, and may have a structure in which the chromium of the source of chromium forms a coordinate bond with the X moiety of the group represented by Chemical Formula 1 Such organic chromium compounds can be applied to catalyst systems for the oligomerization reaction of olefins and thus exhibit excellent catalytic activity and high selectivity to 1-hexene or 1-octane.

In Chemical Formula 1-1, details and specific examples about X and $R_1$ to $R_4$ are the same as described for the ligand compound of Chemical Formula 1.

Meanwhile, according to another aspect of the present invention, there is provided a catalyst system for olefin oligomerization i) comprising a source of chromium, the above-described ligand compound and a cocatalyst; or ii) comprising an organic chromium compound including a group represented by the following chemical formula 1-1, and a cocatalyst.

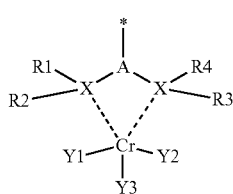

[Chemical Formula 1-1]

in Chemical Formula 1-1,

\* means that the group represented by Chemical Formula 1-1 is a radical,

A is boron (B), nitrogen (N), phosphorus (P) or antimony (Sb), each X is independently phosphorus (P), arsenic (As), or antimony (Sb), $R_1$ to $R_4$ are each independently an aryl group having 6 to 20 carbon atoms in which at least one substituent selected from the group consisting of an alkyl group, an alkoxy group, an alkylsulfanyl group and an alkylsilyl group is optionally substituted or bonded at the meta or para position;

Cr is chromium, and $Y_1$ to $Y_3$ are each independently a halogen, a hydrogen, a hydrocarbyl having 1 to 10 carbon atoms, or a heterohydrocarbyl having 1 to 10 carbon atoms.

Details and specific examples about the ligand compound and the organic chromium compound are the same as disclosed above.

According to one embodiment, the catalyst system for olefin oligomerization may be i) a tricomponent catalyst system including a source of chromium, the above-described ligand compound, and a cocatalyst, or ii) a bicomponent catalyst system including the above-described organic chromium compound and a cocatalyst.

In the catalyst system, the source of chromium may be an organic or inorganic chromium compound having an oxidation state of chromium of 0 to 6, and examples thereof include a chromium metal, or a compound in which any organic or inorganic radical is bonded to chromium. Here, the organic radicals may be alkyl, alkoxy, ester, ketone, amido, carboxylate radicals having 1 to 20 carbon atoms per radical, and the inorganic radicals may be halides, sulfates, oxides, and the like.

Preferably, the source of chromium is a compound which can exhibit a high activity for oligomerization of olefins and which is easily usable and available. The source of chromium may be at least one compound selected from the group consisting of chromium (III) acetylacetonate, chromium (III) chloride tetrahydrofuran, chromium (III) 2-ethylhexanoate, chromium (III) acetate, chromium (III) butyrate, chromium (III) pentanoate, chromlum (III) laurate, chromium (III) tris(2,2,6,6-tetramethyl-3,5-heptenedionate), and chromium (III) stearate.

Preferably, the cocatalyst is an organic metal compound including a Group 13 metal, and any cocatalyst can be used without particular limitation as long as it is any compound which can be generally used for polymerizing an olefin in the presence of a catalyst of a transition metal compound.

For example, the cocatalyst may be at least one compound selected from the group consisting of compounds represented by the following chemical formulas 4 to 6:

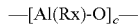—[Al(Rx)-O]$_c$—         [Chemical Formula 4]

in Chemical Formula 4, Rx is the same or different and is each independently a halogen radical, a hydrocarbyl radical having 1 to 20 carbon atoms, or a hydrocarbyl radical having 1 to 20 carbon atoms substituted with a halogen, and c is an integer of 2 or more,

D(Ry)$_3$         [Chemical Formula 5]

in Chemical Formula 5, D is aluminum or boron, Ry is hydrocarbyl having 1 to 20 carbon atoms or hydrocarbyl having 1 to 20 carbon atoms substituted with halogen,

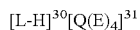[L-H]$^{30}$[Q(E)$_4$]$^{31}$         [Chemical Formula 6]

in Chemical Formula 6,

L is a neutral Lewis base, [L-H]$^+$ is a Bronsted acid, Q is boron or aluminum of a +3 oxidation state, and each E is independently a $C_6$-$C_{20}$ aryl group or a $C_1$-$C_{20}$ alkyl group of which at least one hydrogen is substituted or unsubstituted with a halogen, a $C_1$-$C_{20}$ hydrocarbyl, an alkoxy functional group, or a phenoxy functional group.

According to one embodiment, the compound represented by Chemical Formula 4 may be an alkyl aluminoxane such as methyl aluminoxane, ethyl aluminoxane, isobutyl aluminoxane, butyl aluminoxane, and the like.

According to one embodiment, the compound represented by Chemical Formula 5 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, and so on.

Furthermore, according to one embodiment, the compound represented by Chemical Formula 6 may be triethylammonium tetraphenylborate, tributylammonium tetraphenylborate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetrapentafluorophenylborate, N,N-diethylanilinium tetraphenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylborate, triphenylcarbonium tetraphenylaluminum, triphenylcarbonium tetra(p-trifluoromethylphenyl)borate, triphenylcarbonium tetrapentafluorophenylborate, and so on.

Moreover, as a non-limiting example, the cocatalyst may be an organic aluminum compound, an organic boron compound, an organic magnesium compound, an organic zinc compound, an organic lithium compound, or a mixture thereof. According to one embodiment, the cocatalyst is preferably an organic aluminum compound, more preferably at least one compound selected from the group consisting of trimethyl aluminum, triethyl aluminum, triisopropyl aluminum, triisobutyl aluminum, ethylaluminum sesquichloride, diethylaluminum chloride, ethyl aluminum dichloride, methyl aluminoxane, and modified methyl aluminoxane.

Meanwhile, the content ratio of the components constituting the catalyst system may be determined by considering the catalytic activity and the selectivity to linear alpha-olefins. According to one embodiment, when the catalyst system is a tricomponent catalyst system, it is preferable that the mole ratio of diphosphino aminyl moiety of the ligand compound: the source of chromium: the cocatalyst is controlled to be about 1:1:1 to 10:1:10,000, or about 1:1:100 to 5:1:3,000 Further, when the catalyst system is a bicomponent catalyst system, it is preferable that the mole ratio of diphosphino aminyl moiety of the organic chromium compound to the cocatalyst is controlled to be 1:1 to 1:10,000, or 1:1 to 1:5,000, or 1:1 to 1:3,000.

The components constituting the catalyst system may be mixed at the same time or in an arbitrary order in the presence or absence of a proper solvent and a monomer for acting as an active catalyst system. In this case, the proper solvent may be heptane, toluene, cyclohexane, mehtylcyclohexane, 1-hexene, 1-octene, diethylether, tetrahydrofuran, acetonitrile, dichloromethane, chloroform, chlorobenzene, methanol, acetone, and so on.

Further, according to an embodiment of the present invention, the catalyst system may further include a supporting material. That is, the ligand compound of Chemical Formula 1 may be applied to the oligomerization of ethylene in the form of being supported on the supporting material. The supporting material may be metals, metal salts, metal oxides, or the like, which are commonly applied to a supported catalyst. By way of non-limiting examples, the supporting material may be silica, silica-alumina, silica-magnesia, and the like, and may include oxides, carbonates, sulfates, nitrates of metals such as $Na_2O$, $K_2CO_3$, $BaSO_4$, and $Mg(NO_3)_2$.

Such catalyst system can preferably be used for the tetramerization reaction of ethylene, and it becomes possible to prepare 1-octene with high selectivity as mentioned above.

Meanwhile, according to another aspect of the present invention, there is provided a method for oligomerizing an olefin, comprising the step of carrying out an oligomerization reaction of an olefin in the presence of the above-described catalyst system to form an alpha-olefin.

Preferably, the above oligomerization reaction of olefin can be a tetramerization reaction of ethylene, and may result in the formation of 1-octene as the reaction product.

The method for oligomerization of olefin according to the present invention may be carried out by using an olefin (for example, ethylene) as a raw material and applying the above-mentioned catalyst system and a common device and contact technology. By way of non-limiting examples, the oligomerization reaction of olefin may be carried out by a homogeneous liquid phase reaction in the presence or absence of an inert solvent, by a slurry reaction using the catalyst system that is partially or not totally dissolved, by a bulk reaction in which the alpha-olefin, the product, acts as a main medium, or by a gas phase reaction.

Further, the oligomerization reaction of olefin may be carried out in the presence of an inert solvent. By way of non-limiting examples, the inert solvent may be benzene, toluene, xylene, cumene, chlorobenzene, dichlorobenzene, heptane, cyclohexane, methylcyclohexane, methylcyclopentane, n-hexane, 1-hexene, 1-octene, and so on.

The oligomerization reaction of olefin may be carried out at a temperature of about 0 to about 200° C., or about 0 to about 150° C., about 30 to about 100° C., or about 50 to about 100° C. Furthermore, the reaction may be carried out at a pressure of about 15 to about 3,000 psig, or about 15 to about 1,500 psig, or about 15 to about 1,000 psig.

Hereinafter, the action and effect of the present invention will be described in more detail by way of specific Examples. However, these Examples are given for illustrative purposes only, and the scope of the invention is not intended to be limited by these Examples.

EXAMPLE

In the following, all the reactions were performed using Schlenk technique or a glovebox under argon. The synthesized ligands were analyzed by $^1$H (500 MHz) and $^{31}$P (202 MHz) NMR spectra using a Varian 500 MHz spectrometer. Shift was expressed in ppm, downfield from TMS, with a residual solvent peak as a reference. Phosphorous probe was calibrated with aqueous $H_3PO_4$.

Synthesis of the Ligand Compound

Synthesis Example 1

Synthesis of

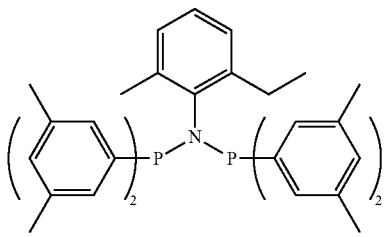

2-ethyl-6-methylaniline (10 mmol) and triethylamine (3 equiv. to amine) were dissolved in dichloromethane (80 mL) under an argon atmosphere. While a flask was immersed in a water bath, chlorobis(3,5-dimethylphenyl)phosphine (20 mmol) was slowly added thereto, and the mixture was stirred overnight. After the solvent was removed under vacuum, diethyl ether, tetrahydrofuran or hexane was added as other solvent to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 49.6 (br m), 53.8 (br m), 61.8 (br s)

Synthesis Example 2

Synthesis of

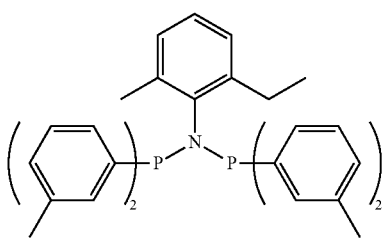

2-Ethyl-6-methylaniline (10 mmol) and triethylamine (3 equiv. to amine) were dissolved in dichloromethane (80 mL) under an argon atmosphere. While a flask was immersed in a water bath, chlorobis(3-methylphenyl)phosphine (20 mmol) was slowly added thereto, and the mixture was stirred overnight. After the solvent was removed under vacuum, diethyl ether, tetrahydrofuran or hexane was added as other solvent to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 56.2 (br s)

Synthesis Example 3

Synthesis of

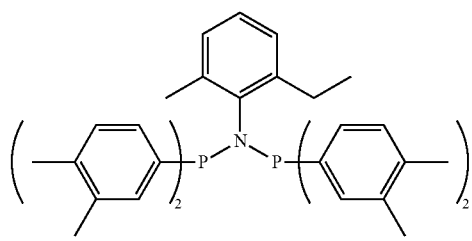

2-Ethyl-6-methylaniline (10 mmol) and triethylamine (3 equiv. to amine) were dissolved in dichloromethane (80 mL) under an argon atmosphere. While a flask was immersed in a water bath, chlorobis(3,4-dimethylphenyl)phosphine (20 mmol) was slowly added thereto, and the mixture was stirred overnight. After the solvent was removed under vacuum, diethyl ether, tetrahydrofuran or hexane was added as other solvent to the mixture, thoroughly stirred and filtered with an air-free glass filter to remove triethylammonium chloride salt. The solvent was removed from the filtrate to yield final product.

$^{31}$P NMR (202 MHz, CDCl$_3$): 50.0 (m)

Synthesis Example 4

Synthesis of

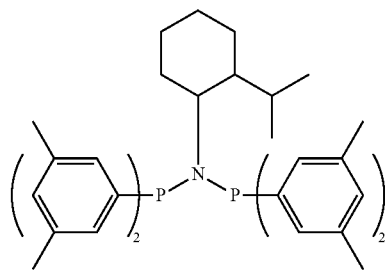

2-Isopropylcyclohexan-1-amine (10 mmol) and triethylamine (3 equiv. to amine) were dissolved in dichloromethane (80 mL) under an argon atmosphere. While a flask was immersed in a water bath, chlorobis(3,5-dimethylphenyl) phosphine (20 mmol) was slowly added thereto, and the mixture was stirred overnight. After the solvent was removed under vacuum, diethyl ether, tetrahydrofuran or hexane was added as other solvent to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 52.3 (s)

Synthesis Example 5

Synthesis of

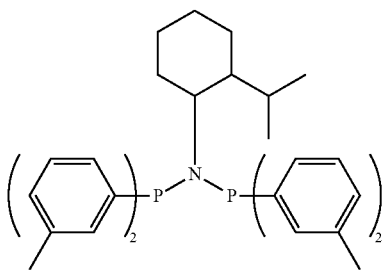

2-Isopropylcyclohexan-1-amine (10 mmol) and triethylamine (3 equiv. to amine) were dissolved in dichloromethane (80 mL) under an argon atmosphere. While a flask was immersed in a water bath, chlorobis(3-methylphenyl)phosphine (20 mmol) was slowly added thereto, and the mixture was stirred overnight. After the solvent was removed under vacuum, diethyl ether, tetrahydrofuran or hexane was added as other solvent to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 51.8 (br s)

Synthesis Example 6

Synthesis of

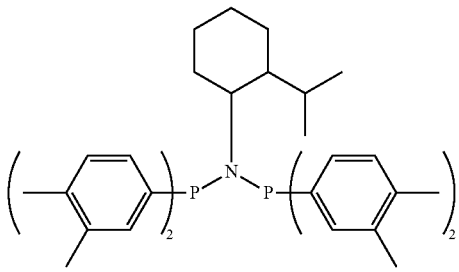

2-Isopropylcyclohexan-1-amine (10 mmol) and triethylamine (3 equiv. to amine) were dissolved in dichloromethane (80 mL) under an argon atmosphere. While a flask was immersed in a water bath, chlorobis(3,4-dimethylphenyl) phosphine (20 mmol) was slowly added thereto, and the mixture was stirred overnight. After the solvent was removed under vacuum, diethyl ether, tetrahydrofuran or hexane was added as other solvent to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 54.5 (br s)

Comparative Synthesis Example 1

Synthesis of

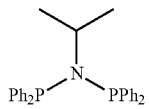

2-Aminopropane (10 mmol) and triethylamine (3 to 10 equiv. to amine) were dissolved in dichloromethane (80 mL) under an argon atmosphere. While a flask was immersed in a water bath, chlorodiphenylphosphine (20 mmol) was slowly added thereto, and the mixture was stirred overnight. After the solvent was removed under vacuum, tetrahydrofuran was added to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 48.4 (br s)

Comparative Synthesis Example 2

Synthesis of

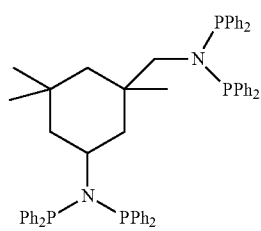

3-(Aminomethyl)-3,5,5-trimethylcyclohexanamine (5 mmol) and triethylamine (3 to 10 equiv. to amine) were dissolved in dichloromethane (80 mL) under an argon atmosphere. While a flask was immersed in a water bath, chlorodiphenylphosphine (20 mmol) was slowly added thereto, and the mixture was stirred overnight. After the solvent was removed under vacuum, tetrahydrofuran was added to the mixture, thoroughly stirred and filtered with an air-free glass filter to remove triethylammonium chloride salt. The solvent was removed from the filtrate to yield a final product.

$^{31}$P NMR (202 MHz, CDCl$_3$): 45.6 (br s), 56.2 (br s)

Preparation of Catalyst System and Progress of Ethylene Oligomerization Reaction

Examples 1 to 6 and Comparative Examples 1 to 2

Chromium (III) acetylacetonate (17.5 mg, 0.05 mmol) and the ligand compound (0.025 mmol) according to Synthesis Examples and Comparative Synthesis Examples were added to a flask under an argon gas atmosphere, to which 10 ml of cyclohexane was added, and the mixture was stirred to prepare a 5 mM (based on Cr) catalyst solution.

A 600 mL Parr reactor was prepared, vacuum was applied at 120° C. for 2 hours, and then, the inside was replaced with argon, and the temperature was decreased to 60° C. After that, 180 ml of cyclohexane and 2 ml of MMAO (isoheptane solution, Al/Cr=1200) were injected, and 0.5 ml (2.5 μmol Cr) of the catalyst solution was injected. The mixture was stirred at 500 rpm for 2 minutes, and then, a valve of an ethylene line adjusted to 60 bar was opened to fill the inside of the reactor with ethylene, followed by removing heat to 45° C., and stirring at 500 rpm for 15 minutes. The ethylene line valve was closed, the reactor was cooled to 0° C. with a dry ice/acetone bath, and then, non-reacted ethylene was slowly vented, and 0.5 ml of nonane (GC internal standard) was injected. After stirring for 10 seconds, 2 mt of the liquid part of the reactor was taken and quenched with water, the obtained organic part was filtered with a PTFE syringe filter to make a GC-FID sample. And, the distribution of liquid product was was analyzed by GC. In addition, to the remaining reaction solution, 400 ml of ethanol/HCl (10 vol % of aqueous 12 M HCl solution) was added, and the mixture was stirred and filtered, and the amount of solids was analyzed. The resulting polymer was dried overnight in a 65° C. vacuum oven.

The results of Examples and Comparative Examples are summarized in table below.

TABLE 1

| | Activity ton/mol Cr/hr | 1-C6 wt % | 1-C8 wt % | C10-C40 wt % | HAO wt % | HAO+ wt % | PE wt % | C6 iso. wt % | C8 iso. wt % | Total wt % |
|---|---|---|---|---|---|---|---|---|---|---|
| Example 1 | 156 | 39.2 | 52.6 | 6.4 | 91.9 | 98.3 | 0.1 | 1 | 0.3 | 99.8 |
| Example 2 | 308 | 35.6 | 56.4 | 5.8 | 92 | 97.7 | 0.2 | 1.4 | 0.4 | 99.7 |
| Example 3 | 212 | 19.2 | 68.6 | 9 | 87.8 | 96.8 | 0.6 | 1.6 | 0.4 | 99.6 |
| Example 4 | 110 | 42.1 | 50.6 | 5.8 | 92.7 | 98.5 | 0.4 | 0.66 | 0.17 | 99.8 |
| Example 5 | 254 | 60.4 | 31.9 | 6.7 | 92.3 | 98.9 | 0.03 | 0.7 | 0.2 | 99.8 |
| Example 6 | 44 | 42.4 | 49.9 | 5.4 | 92.3 | 97.7 | 0.8 | 0.9 | 0.2 | 99.6 |
| Comparative Example 1[a] | 4 | 11.2 | 68.8 | — | 80.7 | — | 0.5 | 4.5 | — | — |
| Comparative Example 2 | 162 | 49.5 | 40.5 | 5.9 | 90 | 95.9 | 1.6 | 1.5 | 0.3 | 99.3 |

Comparative Example 1[a] = 45° C./45 bar,
Cr(acac)$^3$/[cat] = 0.014 mM/Al/Cr = 1200 (MMAO)/60° C./60 bar/15 min Referring to Table 1, it was confirmed that Examples of the present invention exhibited improved selectivity to HAO (higher alpha olefin) as compared with Comparative Examples, and that the content of PE wax, a solid alpha olefin, was decreased.

That is, when an aryl group substituted with a different substituent was included in the diphosphine group of the ligand compound having a specific structure as in the present invention, the selectivity to alpha olefin (1-hexene and 1-octene) could be improved, and the amount of PE wax which is an alpha-olefin and a solid alpha-olefin in the form of an undesirable isomer could be reduced.

The invention claimed is:

1. A ligand compound containing at least one group represented by Chemical Formula 1 in a molecule:

[Chemical Formula 1]

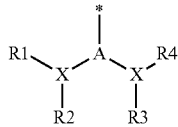

wherein, in Chemical Formula 1,
* means that the group represented by Chemical Formula 1 is a radical,
A is boron (B), nitrogen (N), phosphorus (P) or antimony (Sb),
each X is independently phosphorus (P), arsenic (As), or antimony (Sb),
$R_1$ to $R_4$ are each independently an aryl group having 6 to 20 carbon atoms in which at least one substituent is substituted or bonded at the meta or para position of the aryl group, wherein the at least one substituent is selected from the group consisting of an alkyl group, an alkoxy group, an alkylsulfanyl group and an alkylsilyl group.

2. The ligand compound of claim 1, wherein the at least one substituent is selected from the group consisting of an alkyl group having 1 to 10 carbon atoms, an alkoxy group having 1 to 10 carbon atoms, an alkylsulfanyl group having 1 to 10 carbon atoms, and an alkylsilyl group having 1 to 10 carbon atoms.

3. The ligand compound of claim 1, wherein $R_1$ to $R_4$ in Chemical Formula 1 are each independently a phenyl group having 6 to 20 carbon atoms in total in which only one of the meta positions of the X-linking moiety is substituted or bonded by at least one substituent selected from the group consisting of an alkyl group having 1 to 10 carbon atoms, an alkoxy group having 1 to 10 carbon atoms, an alkylsulfanyl group having 1 to 10 carbon atoms, and an alkylsilyl group having 1 to 10 carbon atoms.

4. The ligand compound of claim 1, wherein $R_1$ to $R_4$ in Chemical Formula 1 are each independently a phenyl group having 6 to 20 carbon atoms in total in which at least two of the meta and para positions of the X-linking moiety is substituted or bonded by at least one substituent selected from the group consisting of an alkyl group having 1 to 10 carbon atoms, an alkoxy group having 1 to 10 carbon atoms, an alkylsulfanyl group having 1 to 10 carbon atoms, and an alkylsilyl group having 1 to 10 carbon atoms.

5. The ligand compound of claim 1, wherein X in Chemical Formula 1 is phosphorus (P), is nitrogen (N) and the moieties represented by $(R^1)(R^2)X—$ and $(R^3)(R^4)X—$ in Chemical Formula I are represented by the following structural formulas:

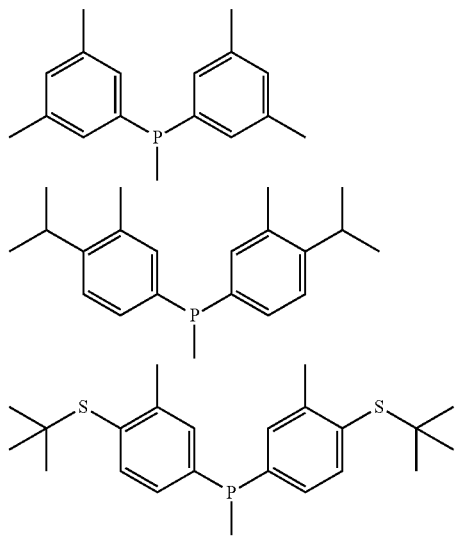

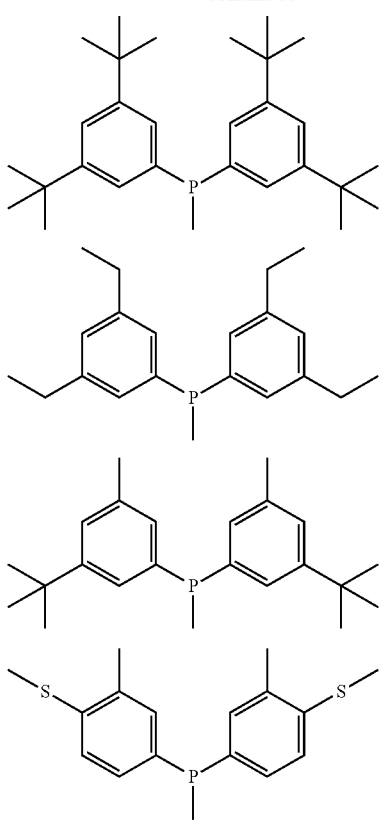

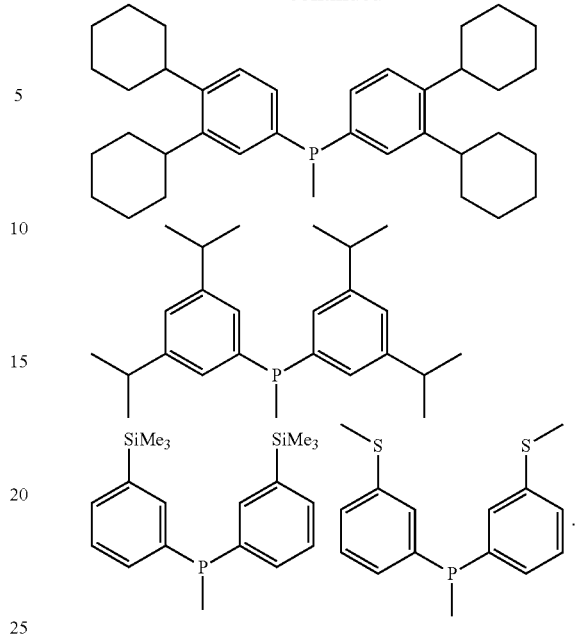

6. An organic chromium compound comprising the ligand compound of claim 1 and chromium (Cr).

7. The organic chromium compound of claim 6, including a group represented by Chemical Formula 1-1:

[Chemical Formula 1-1]

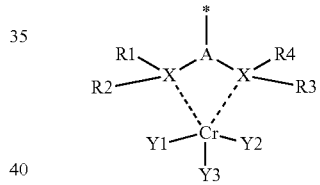

wherein, in Chemical Formula 1-1,

* means that the group represented by Chemical Formula 1-1 is a radical,

A is boron (B), nitrogen (N), phosphorus (P) or antimony (Sb), each X is independently phosphorus (P), arsenic (As), or antimony (Sb), $R_1$ to $R_4$ are each independently an aryl group having 6 to 20 carbon atoms in which at least one substituent is substituted or bonded at the meta or para position of the aryl group, wherein the at least one substituent is selected from the group consisting of an alkyl group, an alkoxy group, an alkylsulfanyl group and an alkylsilyl group;

Cr is chromium, and $Y_1$ to $Y_3$ are each independently a halogen, a hydrogen, a hydrocarbyl having 1 to 10 carbon atoms, or a heterohydrocarbyl having 1 to 10 carbon atoms.

8. A catalyst system for olefin oligomerization i) comprising a source of chromium, the ligand compound of claim 1 and a cocatalyst; or ii) comprising an organic chromium compound including a group represented by Chemical Formula 1-1, and a cocatalyst:

[Chemical Formula 1-1]

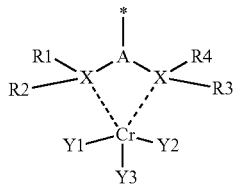

wherein, in Chemical Formula 1-1,

* means that the group represented by Chemical Formula 1-1 is a radical,

A is boron (B), nitrogen (N), phosphorus (P) or antimony (Sb), each X is independently phosphorus (P), arsenic (As), or antimony (Sb), $R_1$ to $R_4$ are each independently an aryl group having 6 to 20 carbon atoms in which at least one substituent is substituted or bonded at the meta or para position of the aryl group, wherein the at least one substituent is selected from the group consisting of an alkyl group, an alkoxy group, an alkylsulfanyl group and an alkylsilyl group;

Cr is chromium, and $Y_1$ to $Y_3$ are each independently a halogen, a hydrogen, a hydrocarbyl having 1 to 10 carbon atoms, or a heterohydrocarbyl having 1 to 10 carbon atoms.

9. The catalyst system for olefin oligomerization of claim 8, wherein the source of chromium includes at least one selected from the group consisting of chromium (III) acetylacetonate, chromium (III) chloride tetrahydrofuran, chromium (III) 2-ethylhexanoate, chromium (III) acetate, chromium (III) butyrate, chromium (III) pentanoate, chromium (III) laurate, chromium (III) tris(2,2,6,6-tetramethyl-3,5-heptenedionate), and chromium (III) stearate.

10. The catalyst system for olefin oligomerization of claim 8, wherein the cocatalyst includes at least one selected from the group consisting of trimethyl aluminum, triethyl aluminum, triisopropyl aluminum, triisobutyl aluminum, ethylaluminum sesquichloride, diethylaluminum chloride, ethyl aluminum dichloride, methyl aluminoxane, and modified methyl aluminoxane.

11. The catalyst system of claim 8 for use in a tetramerization reaction of ethylene.

12. A method for oligomerizing an olefin, comprising the step of carrying out an oligomerization reaction of an olefin in the presence of the catalyst system of claim 8 to form an alpha-olefin.

13. A method for preparing 1-octene, comprising the step of carrying out a tetramerization reaction of ethylene in the presence of the catalyst system of claim 8 to form 1-octene.

* * * * *